United States Patent [19]
Alcock et al.

[11] Patent Number: 5,974,210
[45] Date of Patent: Oct. 26, 1999

[54] PROBE FOR SPECTROSCOPIC ANALYSIS

[75] Inventors: Ian Alcock, Hemel Hempstead; Robert A. Hoult, Beaconsfield, both of United Kingdom

[73] Assignee: Perkin-Elmer Ltd., Beaconsfield, United Kingdom

[21] Appl. No.: 09/004,821

[22] Filed: Jan. 9, 1998

[30] Foreign Application Priority Data

Jan. 15, 1997 [GB] United Kingdom ................... 9700686

[51] Int. Cl.⁶ ..................................................... G02B 6/26
[52] U.S. Cl. ............................. 385/31; 385/34; 385/117; 385/119; 250/227.18; 356/301
[58] Field of Search .................. 385/31, 12, 33, 385/32, 34, 115, 116, 117, 118, 119, 120; 250/227.18, 227.23; 356/301

[56] References Cited

U.S. PATENT DOCUMENTS 5,534,997  7/1996  Schrader ............................... 385/12 X

FOREIGN PATENT DOCUMENTS

| 0358818 | 3/1990 | European Pat. Off. . |
| 0652429 | 5/1995 | European Pat. Off. . |
| 0655221 | 5/1995 | European Pat. Off. . |
| 0711994 | 5/1996 | European Pat. Off. . |
| 01025041 | 1/1989 | Japan . |
| 9209881 | 6/1992 | WIPO . |

*Primary Examiner*—Phan T. H. Palmer
*Attorney, Agent, or Firm*—St.Onge Steward Johnston & Reens LLC

[57] ABSTRACT

A probe for use in spectroscopic analysis comprises an optical fiber with a rod-like end piece. One form of the probe has a local detector which can be deposited on the end piece or located close to it. This improves collection efficiency of radiation diffusely scattered from a sample being investigated. An alternative arrangement uses a local source of radiation.

11 Claims, 1 Drawing Sheet

PROBE FOR SPECTROSCOPIC ANALYSIS

TECHNICAL FIELD

This invention relates to a probe which can be used in spectroscopic analysis.

BACKGROUND ART

Apparatus for carrying out spectroscopic analysis generally includes a source of radiation, typically infrared or near infrared (NIR) radiation, in the case of FT-IR spectroscopy. The Apparatus includes suitable optics for directing the radiation from the source to the location of a sample under investigation and for collecting radiation reflected from or transmitted through the sample for subsequent analysis. It is common in such apparatus to provide an output port to which can be coupled a probe, whereby the probe can be used to receive radiation from the source and direct it to a remote location for carrying out spectroscopic analysis. Such probes generally include one or more optical fibers within which the radiation can propagate. Examples of known probes are described in W092/09881 and EP-A-0652429. In these known arrangements the source of analysing radiation and the detector of the analysing radiation are both located in the main spectrometer housing which means that the analysing radiation has to propagate twice along the length of the fiber or fibres. Such arrangements suffer from poor efficiency in respect of the collection of the diffusely reflected radiation. The present invention is concerned with an improved design of probe.

SUMMARY OF THE INVENTION

According to one aspect of the present invention there is provided a probe for use in spectroscopic analysis comprising an optical fiber and an end piece optically coupled to an output end of the optical fibre, said end piece being generally rod-like and having a diameter greater than that of the fibre, said end piece being so configured and arranged that radiation transmitted from a radiation source to a radiation detector propagates within the end piece between said optical fibre and the annular area of the end piece around the optical fibre end by way of diffuse reflectance from the end face of the end piece remote from the optical fibre, whereby in use when said end face of the end piece is located against a sample the radiation propagating in the end piece is incident on and diffusely reflected from that sample and wherein one of said source and detector is located at or in the vicinity of the end piece.

The radiation may propagate from the fibre end to said annular area. Alternatively, the radiation may propagate from the annular area to the fibre end.

The source of radiation may be at a location remote from the end of the fibre. A detector of radiation may be provided at or near said annular area. Said detector may be of annular form. The detector may be deposited on the annular area.

Alternatively the detector may be deposited on the end face of a tubular sleeve located around the end portion of the fibre so that it is disposed at a position spaced axially from the end face of the fibre.

The end face of the end piece may be radiussed, the arrangement being such that radiation incident thereon and specularly reflected therefrom propagates to a position or area remote from the detector. The radiussing may be such that radiation specularly reflected is caused to be incident on a masked area in the region of the detector.

The end piece may be in the form of a glass rod.

It will be seen that the present design provides a diffuse reflectance probe using a single optical fibre and the design of the end piece with a local radiation source or detector provides efficient collection of radiation reflected from the sample under investigation. It is relatively simple to manufacture and to use.

According to another aspect of the present invention there is provided a probe for use in spectroscopic analysis comprising an optical fibre and an end piece optically coupled to an output end of the optical fibre, said end piece being generally rod-like and having a diameter greater than that of the fibre, said end piece being so configured and arranged that radiation transmitted from a radiation source to a radiation detector propagates within the end piece between said optical fibre and the annular area of the end piece around the optical fibre end by way of diffuse reflectance from the end face of the end piece remote from the optical fibre, whereby in use when said end face of the end piece is located against a sample the radiation propagating in the end piece is incident on and diffusely reflected from that sample wherein the end face of the end piece is radiussed, the arrangement being such that radiation incident thereon and specularly reflected therefrom does not propagate to the detector.

The invention will be described now by way of example only, with particular reference to the accompanying drawings. In the drawings:

DETAILED DESCRIPTION OF THE PREFERRED EMBODIMENTS

Figure 1:
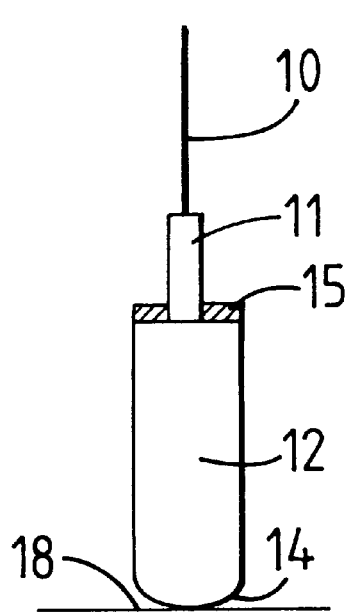
FIG. 1 is schematic illustration of a reflectance probe in accordance with the present invention.

Referring to FIG. 1, a diffuse reflectance probe comprises an optical fibre (10) whose end portion is located within a ferrule (11). The ferrule (11) is preferably radiussed, but could have a planar end face. An end piece (12) in the form of a glass rod is secured to the end of the fibre either by bonding or by spring loading. It is important that there be good optical contact between the end face of the optical fibre (10) and the end face of the glass rod (12) in order to suppress fringes. The rod (12) is generally cylindrical and its end remote from the optical fibre is radiussed as shown at (14). At its other end the rod (12) is formed with a detector (15) of generally annular form. The detector can be formed from any suitable material which can sense the radiation which is used in the investigation and can be deposited on the end face of the rod (12). In infra red spectroscopy the radiation will be in the infra red region of wavelengths. The outer cylindrical surface of the rod (12) should be protected from contamination by, for example, a metallisation layer.

Figure 2:
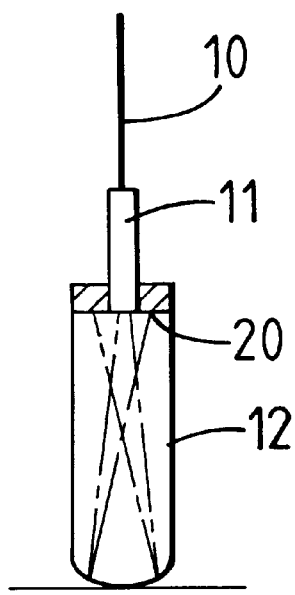
FIG. 2 is a schematic illustration illustrating a modified feature of the arrangement of FIG. 1.

The rod (12) is optically transmitting and its length is so chosen as to allow a beam emanating from the end face of the fibre (10) to diverge slightly and thereby illuminate the sample shown schematically at (18) with a desired spot size. Radiation which is diffusely scattered from the sample is collected by the rod and transmitted by internal reflection to the detector (15) deposited on the end face of the rod. The radiussed portion (14) on the end face of the rod (12) is provided to minimise the amount of specularly reflected radiation which is reflected towards the detector. Minimising this specular reflection increases the absorbance range over which measurements can be carried out. The radius is chosen, and can be angled such that the specularly reflected radiation is directed onto a masked area adjacent the fibre. This masked area is shown by reference numeral (20) in FIG. 2. A modification of this arrangement would be to arrange the fibre (10) slightly off-axis relative to the rod (12) and direct the specularly reflected radiation back onto a masking spot appropriately positioned on the annular end face.

Thus in use the probe is moved close to a sample under investigation and radiation allowed to propagate from a spectrometer (not shown) along the fibre (10) through the rod (12) and onto the sample (18). Radiation diffusely reflected back from the sample is detected by the detector (15), which is coupled to suitable analysing circuitry in the spectrometer to provide suitable data. The design shown in the Figures allows easy interconnection between the fibre and the rod (12) and provides efficient collection of radiation from the sample. When a probe of the present type is used to irradiate a sample, the radiation is diffusely scattered over a wide range of angles which makes efficient collection of that radiation difficult. The use of the detector (15) at or in the vicinity of the rod (12) provides efficient collection of the diffusely scattered radiation.

Figure 3:
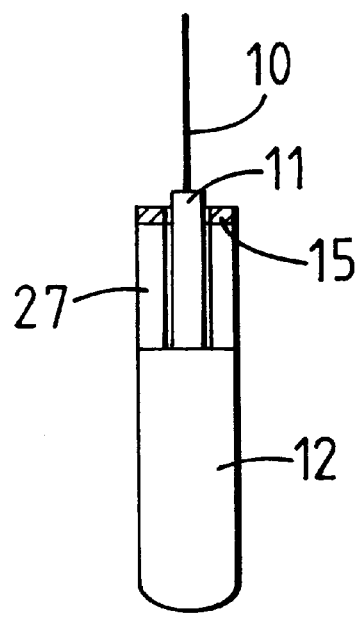
FIG. 3 illustrates another modification.

A modification of the arrangement shown in FIG. 1 is illustrated in FIG. 3 and in this modification the detector is deposited on the end of a tubular sleeve (22) which is disposed around the end portion of the fibre. The sleeve (22) is optically transmitting and can be formed of the same material as the rod (12). In this arrangement the detector is effectively moved further away from the tip of the rod (12).

Another modification which could be used is the provision of a beam splitter or fold mirror which could be used to divert light from the rod through focusing optics onto a separate detector. If a beam splitter were to be used it could have a coating to spectrally separate the beam into different detectors to optimise performance over the spectra range employed.

Another modification would be the provision of a curved window attached to the radiussed end (14) of the rod or a suitable coating such as sapphire, diamond or similar hard material to improve mechanical and chemical durability of the probe.

It is possible to provide probes with differing lengths of rods, thereby allowing different spot sizes to be achieved and optimised for a particular sample type.

A further facility which can be provided is temperature stabilisation of the detector. In order to achieve this a peltier cooler can be bonded to the reverse side of the detector to temperature stabilise or cool the detector if necessary.

Figure 4:
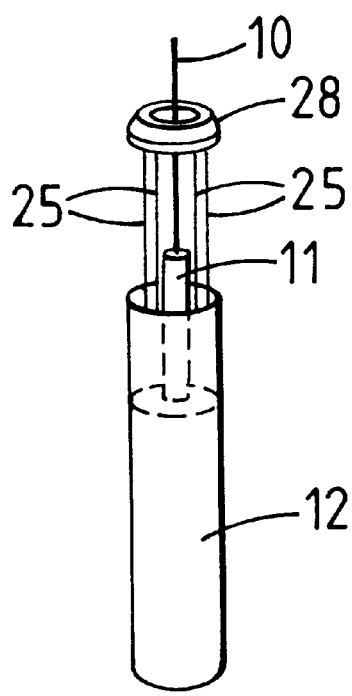
FIG. 4 illustrates a further embodiment of a probe in accordance with the present invention.

In the embodiments described above, the source of radiation is disposed remotely from the probe end piece and typically is located in the spectrometer. The light from that source is propagated along the fibre and reflected from the sample to a detector disposed close the end piece. It is possible to provide an alternative arrangement in which the light source is disposed in the vicinity of the end piece and radiation from the light source is reflected from the sample, collected by the optical fibre and directed back to a detector located at the spectrometer. An arrangement which can achieve this is illustrated in FIG. 4 of the drawings. In this arrangement the end piece (12) includes an axially extending sleeve in a manner similar to that of the arrangement of FIG. 3. A series of annularly spaced optical fibres (25) are optically coupled to the annular end face of the sleeve and can couple radiation from a radiation source (28) into the sleeve, whereby the radiation propagates along the sleeve through the end face so that it is incident on a sample under investigation. Radiation diffusely reflected from the sample is transmitted back along the end piece by internal reflected and collected by the optical fibre (10) which then guides that radiation to a remotely located detector. In order that sufficient diffusely scattered radiation is collected by the fibre (10) it may be necessary to select as a source (28) one which has an appropriate angular distribution of transmitted radiation so that the arrangement operates substantially in reverse to that of for example FIG. 1. One suitable light source is a projector lamp.

An arrangement similar to that of FIG. 4 which employs a bundle of fibres (25) can be used when light propagates initially along the fibre (10) from a source at the end of the fibre, and then is detected by a detector optically coupled to the fibres (25).

Figure 5:
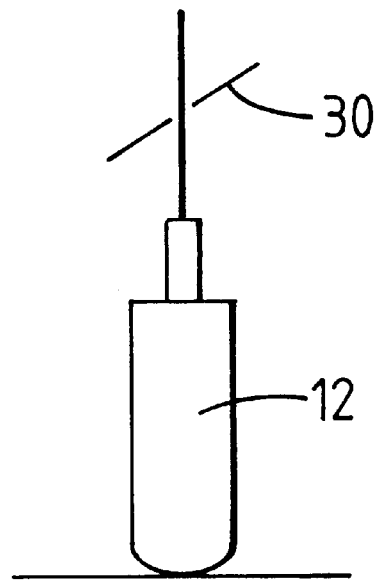
FIG. 5 illustrates a still further embodiment of a probe in accordance with the present invention.

Another modification is illustrated in FIG. 5. In this a fold mirror (30) is located above the rod (12). The mirror has a central aperture through which the fibre (10) can pass. The detector (not shown) is moved to a position in which it can receive radiation reflected from the mirror (30).

The embodiments have been described as using a single fibre (10). It will be appreciated that multiple fibre arrangements can also be employed.

We claim:

1. A probe for use in spectroscopic analysis comprising an optical fibre and an end piece optically coupled to an output end of the optical fibre, said end piece being generally rod-like and having a diameter greater than that of the fibre, said end piece being so configured and arranged that radiation transmitted from a radiation source to a radiation detector propagates within the end piece between said optical fibre and the annular area of the end piece around the optical fibre end by way of diffuse reflectance from the end face of the end piece remote from the optical fibre, whereby in use when said end face of the end piece is located against a sample the radiation propagating in the end piece is incident on and diffusely reflected from that sample and wherein one of said source and detector is located at or in the vicinity of the end piece.

2. A probe according to claim 1 wherein the detector of radiation is provided at or near said annular area.

3. A probe according to claim 2, wherein said detector is of annular form.

4. A probe according to claim 2, wherein the detector is deposited on the annular area.

5. A probe according to claim 1 wherein the source of radiation is at a location remote from the end of the fibre.

6. A probe according to claim 5, wherein the detector is deposited on the end face of a tubular sleeve located around the end portion of the fibre so that it is disposed at a position spaced axially from the end face of the fibre.

7. A probe according to claim 1, wherein the end face of the end piece is radiussed, the arrangement being such that radiation incident thereon and specularly reflected therefrom propagates to a position or area remote from the detector.

8. A probe according to claim 7, wherein the radiussing is such that radiation specularly reflected is caused to be incident on a masked area in the region of the detector.

9. A probe according to claim 1, wherein the radiation propagates from the fibre end to said annular area.

10. A probe according to claim 1, wherein the radiation propagates from the annular area to the fibre end.

11. A probe for use in spectroscopic analysis comprising an optical fibre and an end piece optically coupled to an output end of the optical fibre, said end piece being generally rod-like and having a diameter greater than that of the fibre, said end piece being so configured and arranged that radiation transmitted from a radiation source to a radiation detector propagates within the end piece between said optical fibre and the annular area of the end piece around the optical fibre end by way of diffuse reflectance from the end face of the end piece remote from the optical fibre, whereby in use when said end face of the end piece is located against a sample the radiation propagating in the end piece is incident on and diffusely reflected from that sample wherein the end face of the end piece is radiussed, the arrangement being such that radiation incident thereon and specularly reflected therefrom does not propagate to the detector.

* * * * *